United States Patent [19]

Shippert

[11] Patent Number: 5,507,721
[45] Date of Patent: Apr. 16, 1996

[54] MEDICAL APPARATUS AND METHOD FOR APPLYING PRESSURE AND ABSORBING FLUID

[76] Inventor: Ronald D. Shippert, 4975 S. Albion St., Littleton, Colo. 80121

[21] Appl. No.: 210,664

[22] Filed: Mar. 18, 1994

[51] Int. Cl.$^6$ ............................................. A61F 5/00
[52] U.S. Cl. .................. 602/46; 602/53; 606/201; 604/308
[58] Field of Search ................. 602/46, 52–54, 602/58; 606/201; 604/304, 308; 128/888

[56] References Cited

U.S. PATENT DOCUMENTS

| | | |
|---|---|---|
| 2,387,642 | 10/1945 | Calhoun . |
| 2,858,830 | 11/1958 | Robins . |
| 3,125,093 | 3/1964 | Hutchins . |
| 3,156,242 | 11/1964 | Crowe, Jr. . |
| 3,229,691 | 1/1966 | Crowe, Jr. . |
| 3,824,996 | 7/1974 | Carlisle ................................ 602/53 X |
| 3,954,109 | 5/1976 | Patel . |
| 4,005,709 | 2/1977 | Laerdal ..................................... 602/53 |
| 4,224,945 | 9/1980 | Cohen .................................. 602/53 X |
| 4,534,354 | 8/1985 | Bonner, Jr. et al. . |
| 4,733,659 | 3/1988 | Edenbaum et al. . |
| 4,773,409 | 9/1988 | Cilento et al. ......................... 602/54 X |
| 4,925,187 | 5/1990 | Fleenor et al. ......................... 273/54 B |
| 4,977,892 | 12/1990 | Ewall ....................................... 602/57 |
| 5,092,323 | 3/1992 | Riedel et al. ......................... 602/52 X |

OTHER PUBLICATIONS

"SURESEAL™, Self–Activating Pressure Dressing," Gainor Medical, McDonough, Georgia.

*Primary Examiner*—Linda C. Dvorak
*Attorney, Agent, or Firm*—Sheridan Ross & McIntosh

[57] ABSTRACT

A medical apparatus and method for wound dressing are provided for application with all sizes and shapes of wounds, particularly lacerations and deep and ragged cuts. The medical apparatus includes a compressed pad that expands as it absorbs body fluid from the wound and a backing member that increases the pressure applied to the body part as the compressed pad expands. The medical apparatus applies pressure to the wound of at least 0.4 psi.

19 Claims, 1 Drawing Sheet

MEDICAL APPARATUS AND METHOD FOR APPLYING PRESSURE AND ABSORBING FLUID

FIELD OF THE INVENTION

The present invention relates to wound dressings and more particularly to an apparatus and method for applying pressure to and absorbing body fluid from a wound.

BACKGROUND OF THE INVENTION

It is known to apply bandages having an expandable, absorbent pad to a puncture wound to absorb body fluid from the puncture (hereinafter called "expandable bandages"). In expandable bandages, the absorbent pad expands as the absorbent pad absorbs body fluid to apply an even pressure distribution to the puncture site. Expandable bandages also include a band having an adhesive on one or both ends to secure the absorbent pad to the body part. The absorbent pad can be in a variety of shapes but typically has a narrow length and width for use with puncture wounds.

Expandable bandages have numerous problems. Some types of expandable bandages exert little, if any, hydrostatic pressure on the puncture site as the absorbent pad experiences only a slight amount of expansion during absorption of body fluid. The pressure exerted on the puncture is primarily the pressure, if any, from securing the bandage to the body part. The pressure distribution on the body part is therefore substantially constant, regardless of the volume of body fluid absorbed by the absorbent pad. These bandages not only may fail to exert a sufficient pressure on the puncture site to assist clotting but also may in fact prevent clotting by absorbing the body fluid before the body fluid is able to clot.

Other types of expandable bandages, though having a higher degree of expansion of the absorbent pad than the type of expandable bandage described above, also have certain drawbacks, especially when significant quantities of body fluid are absorbed by the absorbent pad. As the absorbent pad expands, the bandages may experience a decline in the amount of pressure exerted on the puncture. The increasing pressure against the pad has caused deformation of the absorbent pad, overstretching of the band, and/or failure of the adhesive bond securing the bandage to the body part or the absorbent pad to the band.

There is a need for a bandage that can effectively exert a hydrostatic pressure on a breach in a body part to induce clotting of the body fluid.

There is a further need for a bandage that can continuously and effectively exert a hydrostatic pressure on a breach that is sufficient to aid clotting of the body fluid.

There is a further need for a bandage that can absorb the significant quantities of body fluid from types of breaches other than punctures (e.g., lacerations and deep and ragged cuts), which experience greater amounts of body fluid loss than punctures, while exerting continuously against the breach a pressure sufficient to slow bleeding.

SUMMARY OF THE INVENTION

The present invention is a medical apparatus for applying pressure to a body part while absorbing body fluid. The medical apparatus includes a compressed pad for contacting the body part to expand upon body fluid absorption; a backing member overlying the upper face of the compressed pad to increase pressure applied to the body part as the compressed pad absorbs body fluid and expands; and a fastener assembly connected to the backing member for fastening the compressed pad and backing member to the body part.

The medical apparatus is capable of applying a pressure of at least about 0.4 psi to the body part. This pressure represents the maximum pressure exerted by the breach on the compressed pad in virtually all applications of interest. By exerting a pressure of at least about 0.4 psi to the breach, the medical apparatus produces a positive hydrostatic pressure on the breach, thereby significantly enhancing the ability of the body fluid to clot.

The pad is compressed so that it can be expanded by absorption of body fluid. The thickness after absorption is at least about twice the thickness that existed before absorption of body fluid and, preferably, from about 200 to about 300% of the pad thickness that existed before absorption. The compressed pad has a thickness of at least about 0.25 inch up to about 1.5 inches before absorbing any body fluid.

The backing member is sufficiently rigid so that there is no change in the shape or dimension of the backing member during absorption of body fluid by the pad. The backing member has a length and width that does not extend beyond the upper face of the compressed pad. The backing member overlies substantially all portions of the upper face. The thickness of the compressed pad is at least five times greater than the thickness of the backing member.

The present invention provides a method for controlling body fluid escaping from a breach in a body part in which the breach has a length of at least about 1 inch. The method includes providing a compressed pad having a first thickness before absorbing any body fluid; contacting the compressed pad with the body part using a fastening assembly; absorbing body fluid causing at least portions of the compressed pad along its entire first thickness to expand to at least a second thickness which is at least twice the first thickness; and applying a pressure of at least about 0.4 psi after the absorbing step to the body part having the breach.

The providing step can include providing a backing member to the upper face of the compressed pad. The backing member is substantially rigid and has a thickness less than about 20% of the first thickness.

In both embodiments, the compressed pad can have different thicknesses at different locations on the lower face of the pad during absorption of body fluid. The thickness at a selected location on the lower face is directly proportional to the volume of the body fluid absorbed by the compressed pad at the selected location. The maximum thickness of the compressed pad is at the location having the greatest volume of body fluid absorbed by the compressed pad and the minimum thickness is at the location having the least volume of body fluid absorbed by the compressed pad. The pressure exerted by the compressed pad at a certain location is directly proportional to the thickness of the compressed pad at that location.

The various embodiments of the subject invention offer numerous advantages over the prior art, including:

The subject invention exerts a positive, rather than a negative, hydrostatic pressure on a breach in a body part. The subject invention has sufficient strength to exert a greater pressure on the breach than the breach exerts on the compressed pad. The resulting positive hydrostatic pressure significantly enhances clotting of the body fluid.

Certain embodiments of the present invention are capable of being applied not only to punctures but also to other types of breaches. The compressed pad has sufficient absorption capacity to absorb the significantly greater quantities of body fluid typically generated by larger breaches compared to punctures. The embodiments are further capable of resisting the greater pressures exerted by larger breaches on the compressed pad compared to the pressures exerted by punctures on the compressed pad.

During body fluid absorption some embodiments of the compressed pad exert an uneven pressure distribution along the breach. As discussed above, the uneven pressure distribution applies greater pressure to those points along the breach releasing large amounts of body fluid and lesser pressure to those points along the breach releasing small amounts of body fluid. The uneven pressure distribution significantly enhances clotting of the body fluid along the entire length of the breach compared to conventional bandages.

One embodiment of the fastening assembly employs fasteners including hooks and interlocking loops to attach the compressed pad to the body part. Such fasteners are waterproof and able to withstand exposure to the large amounts of body fluid being released by large breaches. Such fasteners further provide for ease of fastening of the compressed pad to the body part. This is particularly advantageous in emergency situations.

In at least some embodiments, the compressed pad and the fastening assembly do not adhere to skin and the surface of the breach. Consequently, removal of the compressed pad from the breach is neither as painful nor destructive as many existing bandages.

DETAILED DESCRIPTION

Figure 1:
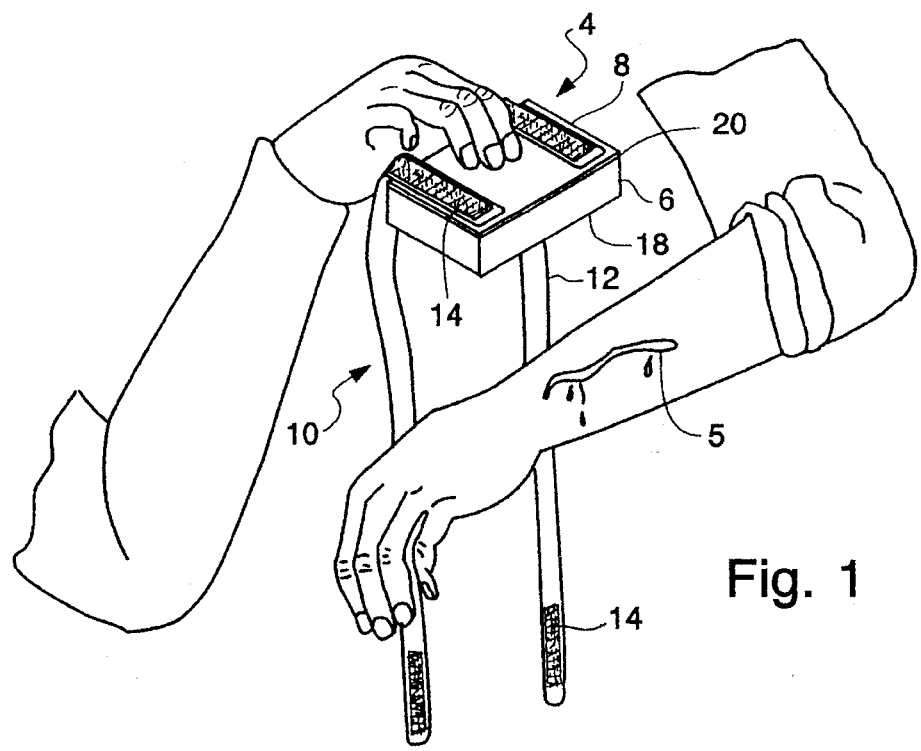
FIG. 1 is a perspective view of one embodiment of the present invention being applied to a breach in a body part.

The present invention is a medical apparatus for absorbing body fluid and exerting pressure, and preferably applying a variable pressure distribution, to a breach in a body part in response to the absorption by portions of a compressed pad of different amounts of body fluid from the breach. The medical apparatus includes a compressed pad for contacting the body part, a backing member on the upper face of the pad, and a fastener assembly connected to the backing member. The present invention is applicable not only to punctures but also to a wide variety of larger breaches, such as lacerations and deep and ragged cuts.

The medical apparatus is based in part upon the recognition that a bandage to be effective should be capable of applying a pressure to a breach in excess of the pressure exerted by the breach on the bandage. In that event, a positive pressure will be exerted on the breach and the ability of the body fluid to clot will be significantly enhanced. As will be appreciated, negative hydrostatic pressures, like those exerted by many types of conventional bandages, can prevent clotting by drawing body fluid from the breach before clotting can occur.

The pressure exerted on a bandage by the breach is a function of a number of factors, including the size of the blood vessel ruptured by the breach and the size and shape of the breach itself. It has been found that for the apparatus of the present invention to be properly operative with the variety of breaches, the apparatus must exert a pressure on the breach of at least about 0.4.

The compressed pad of the medical apparatus has an upper face and a lower face and expands and exerts increasing pressure on the breach as the compressed pad absorbs body fluid. The degree of expansion is directly proportional to the amount of body fluid absorbed by the compressed pad. The hydrostatic pressure exerted by the compressed pad on the breach is directly related to the degree of expansion of the compressed pad. Accordingly, the magnitude of the hydrostatic pressure exerted by the compressed pad on the breach is directly related to the amount of body fluid absorbed by the compressed pad.

The composition of the compressed pad is based on the desired characteristics of the compressed pad. Important characteristics of the compressed pad include the compressed pad's absorption characteristics, the hydrostatic pressure exerted by the compressed pad on the breach and the compressed pad's compression capacity.

Concerning the first factor, the compressed pad's absorption characteristics, the compressed pad should be able to absorb the quantities of body fluids generated by large breaches such as lacerations and deep and ragged cuts. The rate of absorption should be sufficient to absorb body fluids at the rate that body fluids are generated by the breach.

Concerning the second factor, the hydrostatic pressure exerted by the compressed pad on the breach, it is important that the hydrostatic pressure exerted by the compressed pad on the breach at any point in time be more than the contemporaneous pressure exerted by the breach on the compressed pad. If the pressure exerted by the breach on the compressed pad is greater than that exerted contemporaneously by the compressed pad on the breach, a negative hydrostatic pressure will result. As noted above, the negative hydrostatic pressure can negatively impact the ability of the body fluids to clot.

Concerning the last factor, the compressed pad's compression capacity, it is important that the compressed pad be capable of both compression to an amount sufficient to produce the desired hydrostatic pressure at full expansion and retention of the degree of compression before use. As will be appreciated, the amount of hydrostatic pressure exerted on the breach by the compressed pad at full expansion is directly proportional to the initial degree of compression of the compressed pad. Preferably, the compressed pad is compressed so that its thickness expands due to absorption of the body fluid to at least about 200% and, preferably, from about 200 to about 300% of the thickness that existed before absorption of the body fluid.

The compressed pad may be composed of any material that satisfies the factors referred to above. Additionally, the material should contain no substances that may adversely impact the patient. Preferably, the compressed pad is substantially composed of polyvinyl alcohol (PVA), including PVA foam.

The compressed pad can be in a variety of shapes depending on the application and the size and shape of the breach (e.g., whether the breach is a puncture, laceration, cut, etc.) The shape includes, for example, circular, rectangular, and elliptical.

The dimensions of the lower face of the compressed pad vary depending upon the size and shape of the breach to be treated by the compressed pad. By way of example, a compressed pad to treat a puncture can be narrow and short while a compressed pad for a laceration should be wide and long. The apparatus of the present invention is particularly useful in treating breaches of more than about 1 inch in length with ragged edges. To treat such injuries, the compressed pad preferably has a length of about 30%–50% greater than the length of the breach. These dimensions should be sufficient to encompass most lacerations, even if they have irregular shapes or ragged edges.

The thickness of the compressed pad before absorbing body fluid varies depending upon the amount of body fluid to be absorbed by the compressed pad and the desired degree of compression of the compressed pad. Preferably, the compressed pad has a thickness before absorbing body fluid of about 0.5 inch.

The medical apparatus also includes a backing member on the upper face of the compressed pad. The backing member is substantially rigid. The backing member increases the pressure on the body part by reducing pressure losses laterally (in a plane parallel to the lower face) and upwardly (in a plane perpendicular to the lower face) during compressed pad expansion. Preferably, the torsional rigidity and shear strength of the backing member is at least sufficient to resist the pressure exerted by the breach on the compressed pad. More preferably, the backing member has a sufficient torsional rigidity and sheer strength to resist not only the pressure applied to the compressed pad by the breach but also the pressure applied against the breach by the compressed pad. It is desired that the backing member have a rigidity factor that is at least 10 times greater than the rigidity factor of the compressed pad.

The interaction of the backing member and the compressed pad as body fluid is absorbed can cause the compressed pad to have different thicknesses at different locations on the compressed pad's lower face during body fluid absorption. As discussed above, the pressure exerted by the compressed pad at a selected location on the lower face is directly proportional to the thickness of the compressed pad at that location, which is in turn directly proportional to the volume of body fluid absorbed by the compressed pad at that location. The greatest thickness of the compressed pad is at the location having the greatest volume of body fluid absorbed by the compressed pad and the least thickness is at the location having the least volume of body fluid absorbed by the compressed pad. At full absorption, the compressed pad has a substantially uniform thickness at all selected locations on the lower face. Accordingly, at full absorption the compressed pad exerts a substantially uniform pressure at all selected locations on the lower face.

The ability of the compressed pad to exert a variable distribution in response to variable amounts of body fluid absorption at various locations on the lower face significantly enhances clotting of the body fluid at the breach. The greater is the pressure at a point on the breach, the greater is the likelihood that the clotting will occur at that point. As noted above, the pressure at a specific location along the breach will depend upon the rate at which body fluid is emanating from the breach at that location. For example, greater pressure is applied at points along the breach with more bleeding and less pressure at points with less or no bleeding. Accordingly, clotting is significantly enhanced over bandages that apply an even pressure distribution along the breach regardless of the amount of bleeding at a specific point on the breach. The pressure exerted by an even pressure distribution at a selected point will be no larger than the pressure exerted at the point of least compressed pad expansion.

The length and width of the backing member should be sufficient to overlie substantially all portions of the upper face. More preferably, the backing member has a length and width that does not extend beyond the upper face. In other words, the length and width of the backing member are more preferably substantially the same as the length and width of the compressed pad.

The thickness of the backing member should be sufficient to provide the desired torsional rigidity and shear strength discussed above. Preferably, the backing member should have a thickness of at least $\frac{1}{16}$ inch. The thickness of the backing member should also be less than about 20% of the compressed pad thickness that existed before absorption.

The backing member is preferably substantially composed of a water-resistant material having the desired shear strength and torsional rigidity. More preferably, the backing member is substantially composed of a rigid plastic. The backing member, like the compressed pad, can be in a variety of shapes, including circular, rectangular, and elliptical. Preferably, the backing member has generally the same shape as the compressed pad.

The medical apparatus includes a fastener assembly connected to the backing member to fasten the compressed pad and the backing member to the body part. The fastener assembly, like the backing member, should have sufficient strength to resist the pressure exerted on the compressed pad by the breach. More preferably, the fastener assembly should have a sufficient strength to resist not only the pressure applied to the compressed pad by the breach but also the pressure applied against the breach by the compressed pad. In one embodiment, the fastener assembly includes a strap connected to the backing member. The strap should be substantially nonelastic.

FIG. 1 depicts a preferred embodiment of the medical apparatus 4 of the subject invention being applied to a breach 5 in an arm. The medical apparatus 4 includes a compressed pad 6, backing member 8, and fastening assembly 10.

The upper face 20 of the compressed pad 6 is attached to the lower face of the backing member 8 and the upper face 22 of the backing member 8 to the fastening assembly 10 by one or more of a variety of connection parts, such as water resistant adhesive. In either case, the strength of the bonds between the backing member 8 and compressed pad 6 and backing member 8 and fastening assembly 10 should be sufficient to resist the pressure exerted by the breach 5 on the compressed pad 6 and more preferably not only the pressure exerted by the breach 5 on the compressed pad 6 but also by the compressed pad 6 on the breach 5.

Because the backing member 8 is made from a different material, it has the property, in one embodiment, of being cut or formed using a material that is different from the material utilized in cutting the pad 6. In this embodiment, after both are cut to the desired size and shape by cutting devices of different materials, they are adhesively joined together.

The fastening assembly 10 includes two straps 12 and strap fasteners 14. As will be appreciated, fastening assembly 10 can include more or fewer straps depending on the size of the compressed pad 6. The dimensions of straps 12 should be sufficient to surround the body part containing the breach.

The strap fasteners 14 may be any water resistant assembly that attaches one end of the strap 12 to the other. Preferably, the strap fastener 14 is a buckle, hooks with interlocking loops (e.g., "VELCRO®"). As an alternative, the straps 12 may also attach to the body part directly. In this case, a water resistant adhesive is used to bond the strap 12 to the body part. This alternative is employed for body parts that are too large or irregularly sized to be surrounded by a strap 12.

Figure 2:
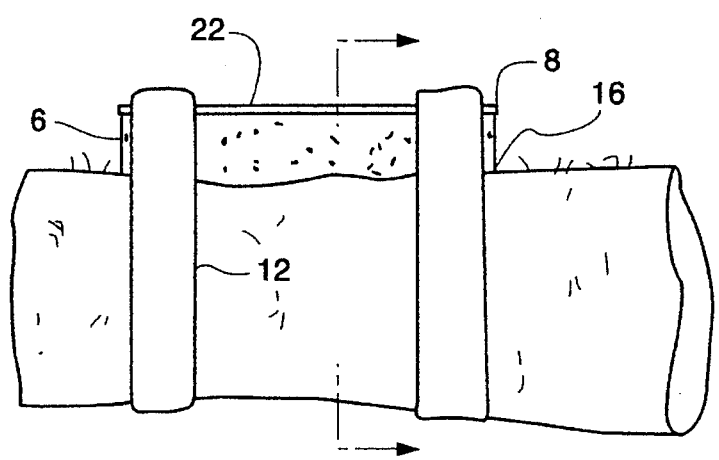
FIG. 2 is a cross-sectional side view of the embodiment applied to a breach in a body part, showing the uneven lower face of the compressed pad in response to variations in body fluid absorption by different portions of the pad.
Figure 3:
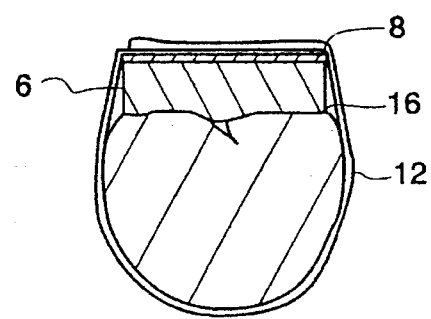
FIG. 3 is a cross-sectional front view of the embodiment applied to a breach in a body part, again showing the uneven lower face of the compressed pad, with the point of greatest pad expansion being at the breach.

As shown in FIGS. 1 through 3, the compressed pad 6 is attached to the body part by locating the compressed pad 6 against the body part and engaging the strap fasteners. After attachment, the compressed pad 6 should be in contact with the body part so that there is essentially no gap or space between the pad 6 and the body part. That is, the compressed pad 6 should be positioned to cover the breach 5 and be in contact with the body part at the breach 5. Body fluid from the breach 5 is absorbed by the compressed pad 6 along the interface between the breach 5 and the compressed pad 6.

As body fluid is absorbed by the compressed pad 6, the thickness of the compressed pad increases and the pressure exerted by the compressed pad 6 on the body part also increases in magnitude. As discussed above, the lower face 16 of the compressed pad 6 is uneven reflecting varying thicknesses of the compressed pad 6 and varying rates of body fluid absorption by the compressed pad 6 along the length of the breach 5. The uneven surface produces a variable pressure distribution along the lower face 18 of the compressed pad 6.

After clotting, the medical apparatus 4 is removed by disengaging the strap fasteners and gently removing the compressed pad 6 from the breach 5. The medical apparatus 4 should be disposed of. As an alternative, the medical apparatus 4 can be designed such that the compressed pad 6 may be replaced and the medical apparatus 4 reused.

While various embodiments of the present invention have been described in detail, modifications and adaptations of those embodiments may occur to those that are knowledgeable in the field. However, it is to be understood that such modifications and adaptations are subject to the scope of the present invention, as set forth in the following claims.

What is claimed is:

1. A medical apparatus for applying pressure to a body part while absorbing body fluid, comprising:
   a compressed pad for contacting a body part, said compressed pad having an upper face and a lower face and said compressed pad expanding upon absorbing body fluid;
   a backing member overlying said upper face and acting to increase pressure applied to the body part as said compressed pad absorbs body fluid and expands; and
   a fastener assembly connected to said backing member for fastening said compressed pad and said backing member to the body part;
   wherein said compressed pad, backing member and fastener assembly collectively apply a pressure of at least about 0.4 psi to the body part when they are attached to the body part, said backing member being rigid and having sufficient rigidity such that said pressure of at least about 0.4 psi is applied during absorbing of body fluid by using solely said collection of said compressed pad, said rigid backing member and said fastener assembly, said compressed pad is compressed so that it is expandable due to absorption of the body fluid to at least about 200 percent of its thickness that existed before absorption of the body fluid, with said thickness expansion occurring against said pressure applied using solely said compressed pad, said rigid backing member and said fastener assembly together.

2. An apparatus, as claimed in claim 1, wherein:
   said compressed pad has a first thickness before absorbing the body fluid and a second thickness after absorbing the body fluid, with said second thickness being in the range of about 200 to about 300 percent of said first thickness.

3. An apparatus, as claimed in claim 1, wherein:
   said compressed pad has a thickness of at least about 0.25 inch up to about 1.5 inch before absorbing any body fluid.

4. An apparatus, as claimed in claim 1, wherein:
   said backing member has a length and a width that does not extend beyond said upper face.

5. An apparatus, as claimed in claim 1, wherein:
   said backing member overlies substantially all portions of said upper face.

6. An apparatus, as claimed in claim 1, wherein:
   said compressed pad has a first thickness and said backing member has a second thickness and in which said first thickness has at least five times greater than said second thickness.

7. An apparatus, as claimed in claim 1, wherein:
   said fastener assembly includes at least a first strap connected to said backing member that is substantially non-elastic.

8. An apparatus, as claimed in claim 7, wherein:
   the fastener assembly includes a second strap spaced from said first strap and connected to said backing member.

9. A medical apparatus for applying pressure and absorbing body fluid, comprising:
   a compressed pad having an upper face and a lower face and said compressed pad expanding upon absorbing body fluid;
   a backing member overlying said upper face acting to increase pressure as said compressed pad absorbs body fluid and expands, said backing member being rigid to provide a desired pressure application; and
   a fastener assembly connected to said backing member for fastening said compressed pad and said backing member to the body;
   wherein said lower face of said compressed pad has dimensions that depend upon the size and shape of an area in the body from which body fluid exits such that said lower face has a first dimension to absorb body fluid from a first body part when the body fluid is exiting the first body part and is differently dimensioned to absorb fluid from a second body part when the body fluid is exiting the second body part, with said compressed pad including a material that absorbs the body fluid and applies pressure to the body while containing the body fluid, and as the body fluid is absorbed said compressed pad has different thicknesses at different locations on said lower face.

10. An apparatus, as claimed in claim 9, wherein:
   said thickness at a selected location on said lower face is directly proportional to the volume of body fluid absorbed by said compressed pad at said selected location.

11. An apparatus, as claimed in claim 9, wherein:
   the maximum thickness is at the location having the greatest volume of body fluid absorbed by said compressed pad and the minimum thickness is at the location having the least volume of body fluid absorbed by said compressed pad.

12. A medical apparatus for applying pressure to a body part while absorbing body fluid, comprising:
   a compressed pad for contacting a body part, said compressed pad having an upper face and a lower face and said compressed pad expanding upon absorbing body fluid;

a backing member overlying said upper face and acting to increase pressure applied to the body part as said compressed pad absorbs body fluid and expands, said backing member has a rigidity factor of at least ten times greater than a rigidity factor of said compressed pad; and a fastener assembly connected to said backing member for fastening said compressed pad and said backing member to the body part;

wherein said compressed pad, backing member and fastener assembly collectively are capable of applying a pressure of at least about 0.4 psi to the body part.

13. A method for controlling body fluid escaping from a breach in a body in which the breach has a length of at least about 1 inch, comprising:

providing a compressed pad having a length of at least about 1.3 inches and a first thickness before absorbing any body fluid, said providing step including providing a rigid backing member to an upper face of said compressed pad;

contacting said compressed pad with the breach using a fastening assembly;

absorbing body fluid causing at least portions of said compressed pad along its entire first thickness to expand to at least a second thickness which is at least twice said first thickness, with said thickness increase occurring due to pressure applied by said rigid backing member, said fastener assembly and said compressed pad; and applying a pressure of at least about 0.4 psi after said absorbing step to the body part having the breach, said step of applying being conducted wherein said pressure is applied substantially solely using a combination of said compressed pad, said rigid backing member and said fastening assembly.

14. A method, as claimed in claim 13, wherein:

said providing step includes providing a backing member to an upper face of said compressed pad with said backing member having a thickness less than about 20% of said first thickness.

15. A method, as claimed in claim 13, wherein:

said fastening assembly includes at least a first strap connected to said backing member.

16. A method, as claimed in claim 13, wherein said providing step includes:

cutting said compressed pad from a panel of polyvinyl alcohol foam using a first cutting device;

cutting a rigid backing member from a panel using a second cutting device; and attaching said backing member to said compressed pad.

17. The method, as claimed in claim 13, wherein:

as body fluid is absorbed by said compressed pad in said absorbing step, said compressed pad exerts different pressures at different locations along said breach.

18. The method, as claimed in claim 17, wherein:

the pressure being exerted by said compressed pad at a selected location along said breach is directly proportional to the volume of body fluid that escapes from said breach during said absorbing step at said selected location.

19. The method, as claimed in claim 17, wherein:

the maximum pressure being exerted by said compressed pad at a location along said breach is at the location at which the greatest volume of body fluid escapes during said absorbing step and the minimum pressure being exerted by said compressed pad at a location along said breach is at the location at which the least volume of body fluid escapes during said absorbing step.

\* \* \* \* \*